(12) United States Patent
Chow et al.

(10) Patent No.: US 10,758,309 B1
(45) Date of Patent: Sep. 1, 2020

(54) METHODS AND SYSTEMS FOR USING COMPUTER-VISION TO ENHANCE SURGICAL TOOL CONTROL DURING SURGERIES

(71) Applicant: Digital Surgery Limited, London (GB)

(72) Inventors: Andre Chow, London (GB); Danail Stoyanov, London (GB); Imanol Luengo Muntion, London (GB); Petros Giataganas, London (GB); Jean Nehme, London (GB)

(73) Assignee: DIGITAL SURGERY LIMITED, London (GB)

( * ) Notice: Subject to any disclaimer, the term of this patent is extended or adjusted under 35 U.S.C. 154(b) by 0 days.

(21) Appl. No.: 16/511,978

(22) Filed: Jul. 15, 2019

(51) Int. Cl.
| | | |
|---|---|---|
| *G05B 13/02* | (2006.01) | |
| *A61B 34/10* | (2016.01) | |
| *G06K 9/62* | (2006.01) | |
| *G06N 20/00* | (2019.01) | |
| *G05B 19/4155* | (2006.01) | |
| *A61F 5/00* | (2006.01) | |
| *A61B 17/32* | (2006.01) | |
| *A61B 17/068* | (2006.01) | |

(Continued)

(52) U.S. Cl.
CPC ............ *A61B 34/10* (2016.02); *A61B 17/068* (2013.01); *A61B 17/320016* (2013.01); *A61B 17/320092* (2013.01); *A61F 5/0076* (2013.01); *G05B 19/4155* (2013.01); *G06K 9/00718* (2013.01); *G06K 9/6262* (2013.01); *G06N 20/00* (2019.01); *A61B 2017/00061* (2013.01); *A61B 2017/00119* (2013.01); *A61B 2017/00199* (2013.01); *A61B 2017/00212* (2013.01); *A61B 2017/320082* (2017.08); *A61B 2017/320095* (2017.08); *A61B 2034/107* (2016.02); *G05B 2219/36414* (2013.01); *G06K 2209/057* (2013.01)

(58) Field of Classification Search
CPC ................................ A61B 34/10; G06N 20/00
USPC .......................................................... 700/28
See application file for complete search history.

(56) References Cited

U.S. PATENT DOCUMENTS 9,123,155 B2    9/2015   Cunningham et al.
9,788,907 B1 *  10/2017  Alvi ....................... G16H 15/00
(Continued)

FOREIGN PATENT DOCUMENTS

CN        101696943 A      4/2010
CN        103142313 B      5/2013
(Continued)

OTHER PUBLICATIONS

U.S. Appl. No. 62/970,808, filed Feb. 6, 2020 to Meglan et al.
(Continued)

*Primary Examiner* — Md Azad
(74) *Attorney, Agent, or Firm* — Cantor Colburn LLP

(57) ABSTRACT

The present disclosure relates to systems and methods that use computer-vision processing systems to improve patient safety during surgical procedures. Computer-vision processing systems may train machine-learning models using machine-learning techniques. The machine-learning techniques can be executed to train the machine-learning models to recognize, classify, and interpret objects within a live video feed. Certain embodiments of the present disclosure can control (or facilitate control of) surgical tools during surgical procedures using the trained machine-learning models.

17 Claims, 6 Drawing Sheets

(51) Int. Cl.
*G06K 9/00* (2006.01)
*A61B 17/00* (2006.01)

(56) References Cited

U.S. PATENT DOCUMENTS

| | | | |
|---|---|---|---|
| 10,152,789 B2 | 12/2018 | Carnes et al. | |
| 10,251,714 B2 | 4/2019 | Carnes et al. | |
| 10,383,694 B1* | 8/2019 | Venkataraman | |
| 2007/0136218 A1* | 6/2007 | Bauer | G06F 19/3481 706/12 |
| 2009/0036902 A1* | 2/2009 | DiMaio | A61B 34/10 606/130 |
| 2012/0020547 A1 | 1/2012 | Zhao et al. | |
| 2013/0288214 A1* | 10/2013 | Kesavadas | G09B 23/285 434/262 |
| 2013/0295540 A1* | 11/2013 | Kesavadas | G09B 23/28 434/262 |
| 2014/0286533 A1* | 9/2014 | Luo | G09B 5/00 382/103 |
| 2014/0350391 A1 | 11/2014 | Prisco et al. | |
| 2015/0297313 A1* | 10/2015 | Reiter | A61B 1/00149 600/408 |
| 2017/0020395 A1 | 1/2017 | Malchano et al. | |
| 2018/0032130 A1 | 2/2018 | Meglan | |
| 2018/0243906 A1 | 8/2018 | Hourtash | |
| 2018/0296075 A1 | 10/2018 | Meglan et al. | |
| 2018/0310811 A1 | 11/2018 | Meglan et al. | |
| 2018/0310875 A1 | 11/2018 | Meglan et al. | |
| 2018/0322949 A1 | 11/2018 | Mohr et al. | |
| 2019/0008587 A1 | 1/2019 | Allison et al. | |
| 2019/0029766 A1 | 1/2019 | Griffiths et al. | |
| 2019/0038362 A1 | 2/2019 | Nash et al. | |
| 2019/0053872 A1 | 2/2019 | Meglan | |
| 2019/0088162 A1 | 3/2019 | Meglan | |
| 2019/0090954 A1 | 3/2019 | Kotian et al. | |
| 2019/0099226 A1* | 4/2019 | Hallen | A61B 34/25 |

FOREIGN PATENT DOCUMENTS

| | | |
|---|---|---|
| JP | 2018/029961 A | 3/2018 |
| WO | 2017/098504 A1 | 6/2017 |
| WO | 2018/005842 A1 | 1/2018 |
| WO | 108024833 A | 5/2018 |
| WO | 2018/217433 A1 | 11/2018 |
| WO | 2018217444 A2 | 11/2018 |
| WO | 2018/237187 A2 | 12/2018 |
| WO | 2019036006 A1 | 2/2019 |
| WO | 2019036007 A1 | 2/2019 |
| WO | 2019050729 A1 | 3/2019 |
| WO | 2019050886 A1 | 3/2019 |
| WO | 2019139949 A1 | 7/2019 |
| WO | 2020009830 A1 | 1/2020 |

OTHER PUBLICATIONS

U.S. Appl. No. 62/945,370, filed Dec. 9, 2019 to Meglan.
U.S. Appl. No. 62/952,628, filed Dec. 23, 2019 to Meglan.
U.S. Appl. No. 62/833,183, filed Apr. 12, 2019 to Meglan et al.
U.S. Appl. No. 62/910,514, filed Oct. 4, 2019 to Meglan et al.

* cited by examiner

METHODS AND SYSTEMS FOR USING COMPUTER-VISION TO ENHANCE SURGICAL TOOL CONTROL DURING SURGERIES

FIELD

The present disclosure generally relates to methods and systems for controlling (or facilitating control of) surgical tools during surgical procedures. More specifically, the present disclosure relates to methods and systems that use computer-vision to facilitate controlling the operation of surgical tools during surgical procedures, thereby improving the safety and reliability of surgeries.

BACKGROUND

Increasingly, cameras are being used to assist surgeons during surgical procedures. For example, laparoscopy is a type of surgery, in which a surgeon makes a small incision near the abdomen of a patient and inserts one or more surgical tools, such as a laparoscope (i.e., a long fiber optic cable connected to a small camera). The laparoscope enables the surgeon to view the affected area in the patient's abdomen. Occasionally, however, the surgical tools can cause injury to the patient due to erroneous handling. Accordingly, there is a need to improve the safety and reliability of the use of surgical tools during surgical procedures.

BRIEF SUMMARY

Certain embodiments of the present disclosure relate to systems and methods that use computer-vision processing systems to improve patient safety during surgical procedures. Computer-vision processing systems may train machine-learning models using machine-learning techniques. For instance, the machine-learning models can be trained to recognize features of surgical tools from images using a data set of sample images. The trained machine-learning models can then be used to interpret new images or video feeds (e.g., images that are not included in the data set of sample images). Certain embodiments of the present disclosure can control (or facilitate control of) surgical tools during surgical procedures using the trained machine-learning models. For instance, certain embodiments may include a camera that is positioned to capture a live video of a surgical procedure. The camera is configured to capture live video within a field of view. The live video feed generated by the camera can be fed into the trained machine-learning model. The machine-learning model is trained, and thus, is configured to recognize patterns or classify objects within image frames of the live video feed. A procedural control system may communicate with the computer-vision processing system to control (or facilitate control of) the surgical tools based on the recognized patterns or classified objects that are outputted from the machine-learning model (e.g., the output being a result of processing the live video feed using the trained machine-learning model). Controlling or facilitating control of surgical tools may include, for example, digitally controlling the energy supplied by a surgical tool, such as a laparoscopic bipolar diathermy energy device (or any other energy device), to supply energy only when the computer-vision processing system automatically recognizes (from the live video feed) that the laparoscopic diathermy energy device is within the field of view of the camera. Otherwise, the computer-vision system can disable the laparoscopic diathermy energy device, so that no power is supplied by the laparoscopic diathermy energy device, thereby disabling the surgical tool from operating outside of the field of view of the camera.

In some implementations, a camera (or any video or image capturing devices) may be positioned in or near a surgery room to capture live video within a field of view. The live video may be of a surgical procedure performed by one or more surgeons (or any other qualified or authorized user) using one or more surgical tools. As only a non-limiting example, the surgical procedure may be a laparoscopic procedure, in which a surgeon operates laparoscopic surgical tools, such as forceps, scissors, probes, dissectors, hooks, retractors, energy devices (either bipolar or monopolar diathermy), ligatures, harmonics, waterjets, and any other suitable surgical tool. The camera may be configured to generate one or more data streams that are transmitted to the computer-vision processing system to be processed using the trained machine-learning model. The one or more data streams may include a sequence of image frames of the live video within the field of view. It will be appreciated that any electronic device that can capture video or a sequence of images can be used herein, and that the present disclosure is not limited to the use of a digital camera.

In some implementations, the computer-vision processing system can receive the one or more data streams and input the received data stream(s) into the machine-learning model. The computer-vision processing system can train the machine-learning model using machine-learning or artificial intelligence techniques (described in greater detail herein). For example, the computer-vision processing system can store a data set of sample images of surgical tools. The machine-learning or artificial intelligence techniques can be applied to the data set of sample images to train the machine-learning model to recognize patterns and classify objects within the images. The trained machine-learning model can then be used to generate an output that, when received at a procedural control system, can cause one or more surgical tools to be controlled.

In some implementations, the control (or facilitated control) of a surgical tool may be automatic. For example, if the procedural control system receives the output from the computer-vision processing system, and if the output indicates that the surgical tool is within the camera's field of view, then the procedural control system can automatically enable the surgical tool to perform a function (e.g., to generate a high frequency electrical signal for diathermy if the surgical tool is a laparoscopic diathermy energy device). As another example, if the output indicates that the surgical tool is not within the camera's field of view or no longer within the camera's field of view, then the procedural control system can automatically disable the surgical tool so as to cease performance of the function (e.g., to control the diathermy energy device to stop supplying energy or to no longer be enabled to perform the function) or at least regulate performance of the function.

In some implementations, the control (or facilitated control) of the surgical tool may be based on user gating. For example, if the output from the computer-vision processing system indicates that the surgical tool is within the camera's field of view, then the procedural control system may output an audible or visible notification for the surgeon performing the surgery. The audible or visible notification may audibly or visibly (respectively) present to the surgeon that the surgical tool is enabled (or disabled) to perform a function. In these implementations, the control of the surgical tool is not automatic, but based on a response or input from the surgeon after the audible or visible notification is presented.

To illustrate and only as a non-limiting example, when a laparoscopic diathermy instrument is detected within the camera's field of view, the procedural control system can cause a speaker to audibly present the words: "Diathermy instrument detected. Please respond with 'OK' to enable instrument."

In some implementations, controlling (or facilitating control) of a surgical tool includes enabling and disabling the functionality of the surgical tool. For example, if the surgical tool is a laparoscopic diathermy energy device, a 400 watt high frequency electrical signal can be supplied by the laparoscopic diathermy energy device when the energy device is detected within the camera's field of view. Conversely, the 400 watt signal is shut off or disabled when the energy device is not detected to be located within the camera's field of view. In some implementations, controlling or facilitating control may include regulating (e.g., modifying by gradually increasing or decreasing) the magnitude of a function. For example, if the surgical tool is a laparoscopic waterjet, the waterjet can automatically be controlled to increase water pressure if the waterjet is detected as being within the field of view. Conversely, if the waterjet is not detected within the field of view, then the water pressure of the waterjet can be reduced. It will be appreciated that the control or facilitated control of the laparoscopic waterjet may be gradual. For instance, the pressure of the waterjet may gradually increase as the waterjet is moved closer to an anatomical structure. Similarly, the pressure of the waterjet may gradually decrease as the waterjet is moved away from the anatomical structure. In some implementations, controlling or facilitating control of the surgical tool may include changing the functionality available to be performed. For example, if the surgical tool is a device with four different possible functions (i.e., functions 1, 2, 3, and 4), the surgical tool may be enabled to only perform functions 1, 2, and 3 when the surgical tool is detected as being within the camera's field of view. Conversely, when the surgical tool is not detected within the camera's field of view, then the surgical tool may be enabled to only perform function 4.

In some implementations, the computer-vision processing system can use the machine-learning model to detect whether a Critical View of Safety (CVS) has been exposed. For example, the CVS is a technique for identifying targets, such as a cystic duct and an artery, during an open cholecystectomy. The computer-vision processing system can detect whether the CVS is detected within the field of view, and whether the application of clips has also been detected within the field of view, and if both are detected, then the surgical tool can be activated near the cystic duct. In any other case, when the surgical tool is near the cystic duct (e.g., but the clips have not been detected), then the surgical tool may be disabled. In these implementations, the machine-learning model may also be trained to detect patterns that can be interpreted as the CVS. The machine-learning model can be trained using a data set of sample images, on which one or more machine-learning algorithms are applied.

In some implementations, the computer-vision processing system may be configured to detect an anatomic structure, in addition to the surgical tool, before enabling the surgical tool to operate. To illustrate and only as a non-limiting example, if the surgical tool is a laparoscopic stapler, then the computer-vision processing system may be configured to detect the pose (e.g., a specific articulation, position, or orientation) of the stapler with respect to the patient's stomach or organ (e.g., liver, duct, kidney, and so on). The computer-vision processing system can enable the laparoscopic stapler to operate its stapling functionality only when the pose is within a defined range (e.g., a range of degrees of freedom from the anatomical structure).

In some implementations, the computer-vision processing system may process a video feed that is generated by a camera embedded in the surgical tool, instead of the camera positioned to capture the surgical procedure. For example, the surgical tool may be a laparoscope, which is connected to or embedded with a camera. A suction device and the laparoscope may be inserted into the patient through a trocar embedded into an incision in the patient. The live video feed from the laparoscope may be processed by the computer-vision processing system. In some implementation, the computer-vision processing system may input the live video feed from the laparoscope into the machine-learning model. The machine-learning model may be trained in advance (and based on a data set of sample images) to detect patterns, such as vapor or hematoma, within the live video feed. If vapor is detected, for example, then the computer-vision processing system may automatically engage the suction device to remove the vapor.

In some implementations, the computer-vision processing system may be configured to detect whether a surgical device is too close to an anatomical structure. For example, if the surgical tool is a phacoemulsification device, the computer-vision processing system may detect whether the device is too close to an iris (e.g., within a threshold distance) based on a comparison of the distance of the device to the anatomical structure and a threshold distance. If the device is detected as being too close to the iris (e.g., within the threshold distance), then the computer-vision processing system can generate an output that, when received at the procedural control system, causes the phacoemulsification device to cease operation.

In some implementations, the computer-vision processing system may be configured to recognize an action occurring within the field of view of the camera. Upon detecting the action, the computer-vision processing system can cause auxiliary surgical tools to be enabled or disabled. To illustrate and only as a non-limiting example, the energy devices used during a laparoscopic cholecystectomy may be disabled when the computer-vision processing system detects that the cystic duct is being clipped.

In some implementations, the computer-vision processing system may be configured to recognize the distance between a critical structure and a surgical tool. The computer-vision processing system can then regulate the magnitude of the energy provided to the surgical tool depending on the proximity of the surgical tool to the critical structure and the surgical tool.

In some implementations, the computer-vision processing system may be configured to recognize the surgeon or other professional assisting with the surgical procedure. Once recognized, the computer-vision processing system can control the surgical tool by modifying configurations or settings of the surgical tool based on a predetermined profile (e.g., preference settings) of the surgeon. For example, a position or physical setting of a surgical tool can be automatically set (based on the preferences of the surgeon) when the computer-vision processing system detects the surgeon's face. Facial recognition techniques may be executed to train the machine-learning model to recognize the surgeon's face.

In some implementations, a system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a computer-implemented method including: collecting a data set including a plurality of images, each image of the plurality of images capturing a portion of a surgical procedure, and the portion of the surgical procedure being performed using a surgical tool. The computer-implemented method also includes training a model using the data set, the model being trained to recognize surgical tools from image data by inputting the data set into one or more machine-learning algorithms. The computer-implemented method also includes receiving one or more data streams, each of the one or more data streams having been generated at and received from an electronic device configured and positioned to capture live video within a field of view during a particular surgical procedure being performed using one or more surgical tools, and the one or more data streams including a sequence of images of the live video within the field of view. The computer-implemented method also includes inputting the one or more data streams into the trained model. The computer-implemented method also includes in response to inputting the one or more data streams into the trained model, detecting a surgical tool from the sequence of images of the one or more data streams, the surgical tool being adapted to perform a function, the detection of the surgical tool being performed by utilizing the model to recognize the surgical tool from the sequence of images of the live video, and the detection of the surgical tool indicating that the surgical tool is within the field of view. The computer-implemented method also includes in response to detecting the surgical tool, facilitating controlling the surgical tool to perform the function, the detection of the surgical tool from the sequence of images of the live video causing the surgical tool to be enabled to perform the function. Other embodiments of this aspect include corresponding computer systems, apparatus, and computer programs recorded on one or more computer storage devices, each configured to perform the actions of the methods.

In some embodiments, a computer-program product is provided that is tangibly embodied in a non-transitory machine-readable storage medium. The computer-program product can include instructions configured to cause one or more data processors to perform operations of part or all of one or more methods disclosed herein.

In some embodiments, a system is provided that includes one or more data processors and a non-transitory computer readable storage medium containing instructions which, when executed on the one or more data processors, cause the one or more data processors to perform operations of part or all of one or more methods disclosed herein.

Advantageously, computer-vision can be used to improve the safety of patients, surgeons, and other medical professionals, according to certain embodiments described herein. Further, as an advantage, the embodiments and implementations described herein can be used with any type of surgical tool in any type of surgery (e.g., in open, laparoscopic, or microscopic operations). Other surgical systems, such as robotic systems, use kinematic analysis for tool control in robotic surgeries. However, those systems are disadvantaged, in that kinematic analysis can only be used when a robotic system is used during the surgical operation.

BRIEF DESCRIPTION OF THE DRAWINGS

The present disclosure will be better understood in view of the following non-limiting figures, in which.

DETAILED DESCRIPTION

Figure 1:
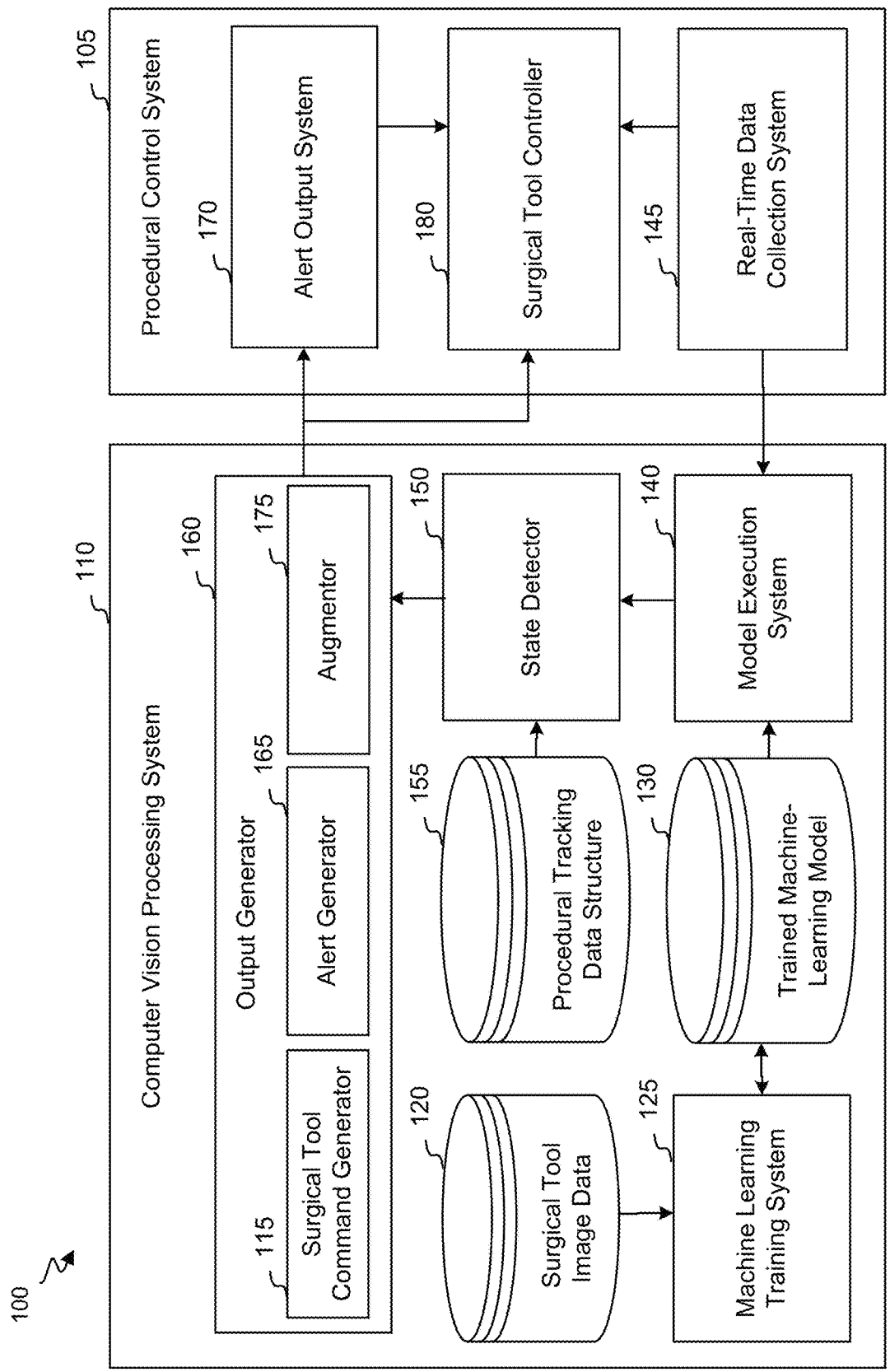
FIG. 1 shows a network for using computer-vision systems to control or facilitate control of surgical tools during a surgical procedure in accordance with some embodiments of the present disclosure.

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

Cameras are increasingly being used during surgical procedures. For instance, cameras can be integrated into surgical tools, such as laparoscopes, or positioned within operating rooms to provide surgeons with alternative viewing angles of a surgery. A camera can capture live video within a defined field of view. According to certain embodiments of the present disclosure, a computer-assisted surgical system can analyze one or more data streams of live video using machine-learning techniques, such as computer-vision, to recognize certain objects (e.g., surgical tools or anatomical structures) within the camera's field of view. The computer-assisted surgical system can interpret information about the surgery using the recognized objects.

Further, the computer-assisted surgical system can be configured to control or facilitate the control of the recognized objects. The control can be determined based on whether or not the object is recognized within the camera's field of view. For example, if the recognized object is a surgical tool detected within the camera's field of view, the computer-assisted surgical system can transmit a signal that causes the surgical tool to enable certain functionality. Otherwise, if the surgical tool is not detected within the camera's field of view, then the computer-assisted surgical system can transmit a signal that disables certain functionality (e.g., turns off the surgical tool). Additional non-limiting examples are provided herein. Advantageously, the computer-assisted surgical system can improve patient safety during surgical procedures, for example, by ensuring that certain functionality (performable by or using the surgical tool) is only enabled when the surgical tool is detected with the camera's field of view.

To illustrate certain embodiments and only as a non-limiting example, a surgeon may perform surgery on a patient to reduce the size of the patient's stomach. The laparoscopic sleeve gastrectomy may involve the use of a laparoscope and a laparoscopic stapler that can staple or suture a portion of the patient's stomach to facilitate removal of that portion. A camera may be positioned within the operating room to capture the surgery. The camera may also be connected to the computer-assisted surgical system. Further, the camera may generate one or more data streams representing a live video feed of the surgery. The live video feed may be received at and processed by the computer-assisted surgical system. A laparoscopic camera housed within the laparoscope may also be configured to transmit one or more data streams of live video to the computer-assisted surgical system.

In advance of the surgery, a machine-learning model may be trained and stored at the computer-assisted surgical system. Training the machine-learning model may include feeding a data set of sample images of various surgical tools, such as laparoscopes and laparoscopic staplers, into the machine-learning model. One or more machine-learning techniques may be executed on the data set of sample images to train the model to recognize features or patterns of surgical tools from the pixels of the sample images. Another machine-learning model or the same machine-learning model may be trained to recognize anatomical structures, such as the patient's liver, certain surgical planes, and risk or avoidance zones (e.g., the so-called "critical view of safety" or "triangle of safety") within a patient's abdomen. Similarly, training this machine-learning model may also include feeding a data set of sample images of anatomical structures to train the model to recognize features or patterns of anatomical structures from the pixels of the sample images. As a result of training the machine-learning model, the machine-learning model may be configured to recognize features or patterns of surgical devices or anatomical structures within image frames of the live video feed.

For the laparoscopic stapler, the protocol may be more complex. The protocol may include a condition that is satisfied when the computer-assisted surgical system recognizes an "avoidance zone" from the live video feed of the laparoscope. For example, when the laparoscope is inserted into the patient, the laparoscope may capture an "avoidance zone" within the laparoscope's field of view. The "avoidance zone" may be a region inside the patient's abdomen, in which the medial margin is the deferent duct and the lateral margin contains the funicular vessels. The "avoidance zone" should not be subject to stapling or suturing. Accordingly, if the computer-assisted surgical system recognizes the "avoidance zone" from the pixels of the live video feed from the laparoscope, then the condition is satisfied. When the condition is satisfied, the computer-assisted surgical system can transmit a signal that (when received at the laparoscopic stapler) causes the laparoscopic stapler to disable the stapling or suturing function. As a technical advantage of the embodiments described herein, the computer-assisted surgical system can automatically ensure that the "avoidance zone" within the patient's abdomen is never stapled or sutured, thereby enhancing patient safety. For instance, when the "avoidance zone" is recognized by the computer-assisted surgical system (using the machine-learning models), the laparoscopic stapler can be controlled to cease or disable operation of the stapling or suturing function. Additional examples are described herein.

Continuing with the above non-limiting example, the computer-assisted surgical system can also automatically personalize settings of surgical tools for the surgeon or other medical professional performing the laparoscopic sleeve gastrectomy. The machine-learning model or another machine-learning model stored at the computer-assisted surgical system may be trained to recognize surgeons or other medical professionals. Training the machine-learning model to recognize surgeons may be achieved by feeding a data set of sample images of each authorized surgeon, so that the machine-learning model can recognize features or patterns of the surgeon from pixels of the sample images. When the computer-assisted surgical system recognizes the surgeon from the image frames within the live video feed of the camera positioned in the operating room, the computer-assisted system may automatically adjust settings of the surgical tools to the predefined preferences of the surgeon. In the example of the laparoscopic sleeve gastrectomy, the surgeon may have a preferred firing speed or clamping force for laparoscopic staplers (e.g., predefined in a surgeon profile). Upon detecting that the surgeon's face is within the camera's field of view, the computer-assisted surgical system may automatically adjust the firing speed or clamping force of the laparoscopic stapler (also detected in the field of view) to the surgeon's preferred settings. The computer-assisted surgical system may store a plurality of surgeon profiles in a database. Each surgeon profile may store one or more predefined preference settings specific to the surgeon. The computer-assisted surgical system can access the stored surgeon profiles and adjust settings of surgical tools detected within the camera's field of view upon also recognizing the surgeon in the field of view. Thus, the control or facilitated control of surgical tools by the computer-assisted surgical system can have the advantageous effect of enhancing patient safety, optimizing surgical tool usage, and improving the overall standard of the surgical process.

In some implementations, the machine-learning model can include (for example) a fully convolutional network adaptation (FCN-VGG) and/or conditional generative adversarial network model configured with one or more hyperparameters to perform image segmentation into classes. For example, the machine-learning model (e.g., the fully convolutional network adaptation) can be configured to perform supervised semantic segmentation in multiple classes—each of which corresponding a particular surgical tool, anatomical structure or body part (e.g., generally or in a particular state), and/or environment. As another (e.g., additional or alternative) example, the machine-learning model (e.g., the conditional generative adversarial network model) can be configured to perform unsupervised domain adaptation to translate simulated images to semantic instrument segmentations.

In some implementations, the computer-assisted surgical system can run one or more machine-learning or artificial intelligence algorithms on the collected data set of sample images to identify patterns between or features of pixels within the collected data set. For example, the machine-learning techniques may include, for example, one or more machine-learning algorithms, such as an ensemble of multi-label classifiers (e.g., supervised or unsupervised learning), artificial neural networks (including backpropagation, Boltzmann machines, etc.), Bayesian statistics (e.g., Bayesian networks or knowledge bases), logistical model trees, support vector machines, information fuzzy networks, Hidden Markov models, hierarchical clustering (unsupervised), self-organizing maps, clustering techniques, and other suitable machine-learning techniques (supervised, semi-supervised, or unsupervised). The detected patterns can be used to define a model that can be used to recognize objects, such as surgical tools, within the sample images. As a non-limiting example, a deep residual network (ResNet) may be used to classify surgical tools or anatomical structures from image pixels of a live video feed.

The trained machine-learning model can then be used in real-time to process one or more data streams (e.g., video streams, audio streams, image data, haptic feedback streams from a laparoscopic surgical tool, etc.). The processing can include (for example) recognizing and classifying one or more features from the one or more data streams, which can be used to interpret whether or not a surgical tool is within the field of view of the camera. Further, the feature(s) can then be used to identify a presence, position and/or use of one or more objects (e.g., surgical tool or anatomical structure), identify a stage or phase within a workflow (e.g., as represented via a surgical data structure), predict a future stage within a workflow, and other suitable features.

FIG. 1 illustrates a computer-assisted surgical system 100 for using one or more machine-learning models to recognize objects, such as surgical tools or anatomical structures, within a live video feed in accordance with some embodiments of the present disclosure. In some implementations, computer-assisted surgical system 100 may include a procedural control system 105 that collects data (e.g., image data, live video streams, and haptic feedback data) and generates outputs responsive to detected objects within the collected data. Procedural control system 105 can include (for example) one or more devices (e.g., one or more user devices and/or servers) located within and/or associated with a surgical operating room and/or control center. Computer-assisted surgical system 100 can further include computer-vision processing system 110 that processes the collected data using a machine-learning model to recognize surgical tools or anatomical structures from live video feed(s) and generate outputs to facilitate controlling the surgical tools. It will be appreciated that computer-vision processing system 110 can include one or more devices (e.g., one or more servers), each of which can be configured to include part or all of one or more of the depicted components of computer-vision processing system 110. In some instances, part of all of computer-vision processing system 110 is hosted in a cloud-based network and/or remote from an operating room and/or physical location corresponding to part or all of procedural control system 105.

In some implementations, computer-vision processing system 110 may include a surgical tool image data store 120 that is configured to store a set of sample or training images to be used to train a machine-learning model. Surgical tool image data store 120 can access an image data set that can include (for example) multiple images and/or multiple videos. The images and/or videos can include (for example) real images and/or video collected during one or more previous procedures (e.g., one or more surgical procedures). For example, the real images and/or video may have been collected by a user device worn by a participant (e.g., surgeon, surgical nurse or anesthesiologist) in the surgery and/or by a non-wearable imaging device located within an operating room, such as a laparoscope. It will be appreciated that the image data set may include sample or training images (e.g., images of surgical tools used for the purpose of training a machine-learning mode) from any data store internal or external to computer-assisted surgical system 100.

Each of the images and/or videos included image data set can be defined as a base image and associated with other metadata that characterizes an associated procedure and/or rendering specifications. For example, the other metadata can identify a type of surgical device, a type of procedure, a location of a procedure, one or more people involved in performing the procedure, and/or an outcome of the procedure. As another (alternative or additional) example, the other metadata can indicate a stage of the procedure with which the image or video corresponds, rendering specification with which the image or video corresponds and/or a type of imaging device having captured the image or video (e.g., and/or, if the device is a wearable device, a role of a particular person wearing the device). As yet another (alternative or additional) example, the other data can include image-segmentation data that identifies and/or characterizes one or more objects (e.g., tools, anatomical objects) that are depicted in the image or video. The characterization can (for example) indicate a position of the object in the image or video (e.g., a set of pixels that correspond to the object and/or a state of the object that is a result of a past or current user handling). It will be appreciated that surgical tool image data store 120 may be configured to collect image data from across a network, such as a hospital network. It will also be appreciated that a data set of images may consist of millions of sample images to improve the accuracy of the machine-learning model.

In some implementations, surgical tool image data image store 120 may store data other than image or video data. As a non-limiting example, surgical tool image data store 120 may be a data structure that can store haptic feedback signals from laparoscopic surgical tools. Haptic feedback can be provided by certain laparoscopic tools to notify surgeons regarding attributes of the material being operated on by an end of the laparoscopic tool. In some implementations, the haptic feedback signals can be combined with the image or video data to facilitate control of surgical tools. As a non-limiting example, computer-assisted surgical system 100 may recognize an "avoidance zone" within a patient's stomach with a confidence of 60%. Computer-assisted surgical system 100 may analyze related haptic feedback signals (being received from the laparoscopic tool or any other tool) to assist in the determination of whether or not the video feed is showing an "avoidance zone" within the camera's field of view. The haptic feedback signal may provide a certain haptic signal detectable by the surgeon when the laparoscopic tool is touching tissue that may indicate a likelihood of being near an "avoidance zone." The present disclosure is not limited to haptic feedback signals. The one or more data streams received from the real-time data collection system 145 may include digital data (e.g., video data) and/or analogue data (e.g., a signal representing a patient's heart rate). For example, the real-time data collection system 145 may be connected to an anesthesia machine that uses sensors to detect the patient's heart rate, pulses, oxygen levels, etc., while generating and mixing gases for the purpose of inducing and maintaining anesthesia. In some examples, pressure sensors may be integrated into the surgical tools to detect an analogue signal representing the pressure applied to the patient's tissue by the surgical tool. The digital or analogue data generated by the sensors can be combined with the video data and processed by the model execution system 140. Advantageously, processing analogue data together with the video data stream provides a more robust assessment of the surgical procedure. In some implementations, the data stream of the video feed can be analyzed to determine a level of force or pressure applied to an anatomical structure. For example, the computer-vision processing system 110 can infer an amount of force that the surgical tool is applying to a patient's tissue by analyzing the degree of deformation or indentation of the tissue. The greater the deformation of the tissue caused by the surgical tool, the greater the amount of force applied to the tissue. In these examples, haptic feedback signals would not be necessary because the force or pressure calculations can be based on video data (e.g., capturing an indentation or deformation of tissue caused by the surgical tool and calculating the amount of force based on the intensity of the indentation or deformation).

Machine learning training system 125 can use the set of sample or training images to train a machine-learning model to recognize and classify surgical tools or anatomical structures. The machine-learning model can be defined based on a type of model and a set of hyperparameters (e.g., defined based on input from a client device). The machine-learning model can be configured based on a set of parameters that can be dynamically defined based on (e.g., continuous or repeated) training (i.e., learning). Machine learning training system 125 can be configured to use an optimization algorithm to define the set of parameters to (for example) minimize or maximize a loss function. The set of (learned) parameters can be stored at trained machine-learning model data structure 130, which can also include one or more non-learnable variables (e.g., hyperparameters and/or model definitions).

In some implementations, machine-learning training system 125 can run one or more machine-learning or artificial intelligence algorithms on the collected data set of sample images stored in surgical tool image data store 120. Running the machine-learning or artificial intelligence algorithms on the data set of images can train the machine-learning model to recognize patterns between of pixels within the collected data set. For example, the machine-learning techniques may include, for example, one or more machine-learning algorithms, such as an ensemble of multi-label classifiers (e.g., supervised or unsupervised learning), artificial neural networks (including backpropagation, Boltzmann machines, etc.), Bayesian statistics (e.g., Bayesian networks or knowledge bases), logistical model trees, support vector machines, information fuzzy networks, Hidden Markov models, hierarchical clustering (unsupervised), self-organizing maps, clustering techniques, and other suitable machine-learning techniques (supervised, semi-supervised, or unsupervised). The detected patterns can be used to define a model that can be used to recognize objects, such as surgical tools, within the sample images. As a non-limiting example, a deep residual network (ResNet) may be used to classify surgical tools or anatomical structures from image pixels of a live video feed.

In some implementations, various object recognition techniques may be used to detect objects from the images stored in surgical tool image data store 120. Non-limiting examples of object recognition techniques that may be executed to recognize objects may include edge detection, feature extraction by primal sketch, histogram analysis, gradient matching, and any other suitable technique.

A model execution system 140 can access trained machine-learning model data structure 130 and accordingly configure a machine-learning model. The machine-learning model can include, for example, a fully convolutional network adaptation or an adversarial network model or other type of model as indicated in data structure 130. The machine-learning model can be configured in accordance with one or more hyperparameters and the set of learned parameters.

The machine-learning model can be configured to receive, as input, image data (e.g., an array of intensity, depth and/or RGB (red, green, blue) values) for a single image or for each of a set of frames represented in a video. The image data can be received from a real-time data collection system 145, which can include (for example) one or more devices (e.g., cameras) located within an operating room and/or streaming live imaging data collected during performance of a procedure.

The machine-learning model can be configured to detect and/or characterize objects within the image data. The detection and/or characterization can include segmenting the image(s). In some instances, the machine-learning model includes or is associated with a preprocessing (e.g., intensity normalization, resizing, etc.) that is performed prior to segmenting the image(s). An output of the machine-learning model can include image-segmentation data that indicates which (if any) of a defined set of objects are detected within the image data, a location and/or position of the object(s) within the image data, and/or state of the object.

State detector 150 can use the output from execution of the configured machine-learning model to identify a state within a surgical procedure that is then estimated to correspond with the processed image data. Procedural tracking data structure 155 can identify a set of potential states that can correspond to part of a performance of a specific type of procedure. Different procedural data structures (e.g., and different machine-learning-model parameters and/or hyperparameters) may be associated with different types of procedures. The data structure can include a set of nodes, with each node corresponding to a potential state. The data structure can include directional connections between nodes that indicate (via the direction) an expected order during which the states will be encountered throughout an iteration of the procedure. The data structure may include one or more branching nodes that feeds to multiple next nodes and/or can include one or more points of divergence and/or convergence between the nodes. In some instances, a procedural state indicates a procedural action (e.g., surgical action) that is being performed or has been performed and/or indicates a combination of actions that have been performed. In some instances, a procedural state relates to a biological state of a patient.

Each node within the data structure can identify one or more characteristics of the state. The characteristics can include visual characteristics. In some instances, the node identifies one or more surgical tools that are typically in use or availed for use (e.g., on a tool try) during the state, one or more roles of people who are performing typically performing a surgical task, a typical type of movement (e.g., of a hand or tool), etc. Thus, state detector 150 can use the segmented data generated by model execution system 140 (e.g., that indicates) the presence and/or characteristics of particular objects within a field of view of a camera) to identify an estimated node to which the real image data corresponds. Identification of the node (and/or state) can further be based upon previously detected states for a given procedural iteration and/or other detected input (e.g., verbal audio data that includes person-to-person requests or comments, explicit identifications of a current or past state, information requests, etc.).

In some implementations, video streams from a previous surgical procedure can be processed (e.g., using image-segmentation) to identify, detect, and determine probabilities of a surgical procedure. The video streams can be annotated to include information relevant to different portions of the surgical procedure to generate surgical data structures. For example, a video stream from an endoscopic procedure can be segmented to identify surgical tools used during the procedure. A surgical data structure can be generated by using training data with pixel-level labels (i.e., full supervision) from the segmented endoscopic procedure video stream. In some implementations, generating a surgical data structure can be produced using other methods. For example, a video stream from an endoscopic procedure can be processed to detect instruments by using three different processes: identification (e.g., identifying which instrument is present in the image), bounding box regression (e.g., localizing each instrument in the image by finding a bounding box that encloses them), and heat map regression (e.g., probability maps of where instruments might be present). This information can be compiled to generate a surgical data structure.

An output generator 160 can use the state to generate an output. Output generator 160 can include an alert generator 165 that generates and/or retrieves information associated with the state and/or potential next events. For example, the information can include details as to warnings and/or advice corresponding to current or anticipated procedural actions. The information can further include one or more events for which to monitor. The information can identify a next recommended action.

The alert can be transmitted to an alert output system 170, which can cause the alert (or a processed version thereof) to be output via a user device and/or other device that is (for example) located within the operating room or control center. The alert can include a visual, audio or haptic output that is indicative of the information.

Output generator 160 can also include an augmentor 175 that generates or retrieves one or more graphics and/or text to be visually presented on (e.g., overlaid on) or near (e.g., presented underneath or adjacent to) real-time capture of a procedure. Augmentor 175 can further identify where the graphics and/or text are to be presented (e.g., within a specified size of a display). In some instances, a defined part of a field of view is designated as being a display portion to include augmented data. In some instances, the position of the graphics and/or text is defined so as not to obscure view of an important part of an environment for the surgery and/or to overlay particular graphics (e.g., of a tool) with the corresponding real-world representation.

Augmentor 175 can send the graphics and/or text and/or any positioning information to an augmented reality device (not shown), which can integrate the (e.g., digital) graphics and/or text with a user's environment in real time. The augmented reality device can (for example) include a pair of goggles that can be worn by a person participating in part of the procedure. It will be appreciated that, in some instances, the augmented display can be presented at a non-wearable user device, such as at a computer or tablet. The augmented reality device can present the graphics and/or text at a position as identified by augmentor 175 and/or at a predefined position. Thus, a user can maintain real-time view of procedural operations and further view pertinent state-related information.

It will be appreciated that multiple variations are contemplated. For example, a machine-learning model may be configured to output a procedural state instead of segmentation data and/or indications as to what objects are being present in various images. Thus, model execution system 140 can (e.g., in this example) include state detector 150.

In some implementations, output generator 160 can also include surgical tool command generator 115, which may be configured to generate output commands that (when received at procedural control system 105 or at the surgical tool itself) cause the surgical tool to be controlled. Non-limiting examples of controlling a surgical tool may include turning on the surgical tool (e.g., energizing the tool), turning off the surgical tool (e.g., de-energizing the tool), enabling the surgical tool to be capable of performing one or more functions, disabling the surgical tool so that the tool is not capable of performing one or more functions, increasing a magnitude or amplitude of a function being performed, decreasing the magnitude or amplitude of a function being performed, changing a primary function being performed to a secondary function (or vice versa), and any other suitable type of control. Output generator 160 may transmit the command for controlling the surgical tool to surgical tool controller 180. Surgical tool controller 180 may include one or more devices configured to transmit the command signals directly to each surgical tool. For instance, the one or more devices of surgical tool controller 180 may be physically attached to each individual surgical tool. When surgical tool controller 180 receives a command signal, surgical tool controller 180 may communicate with the one or more devices physically attached to the surgical tool to control the surgical tool in accordance with the received command. As a non-limiting example, a blocking device may be operable to physically block a laparoscopic diathermy energy device from supplying energy (e.g., by blocking or temporarily creating an open circuit like a switch and/or closing the open circuit to supply energy), or in the case of regulating control, the blocking device may be a regulator configured to incrementally control an amount of energy supplied. If surgical tool controller 180 transmits a command signal to disable the laparoscopic diathermy energy device, then the blocking device may be engaged, and thus, block the energy device from supplying energy. In some implementations, each surgical tool may be specially designed to include a control switch that communicates with surgical tool controller 180. When the control switch is engaged, then the surgical tool may be enabled (or disabled) or the magnitude of the function may be regulated.

Figure 2:
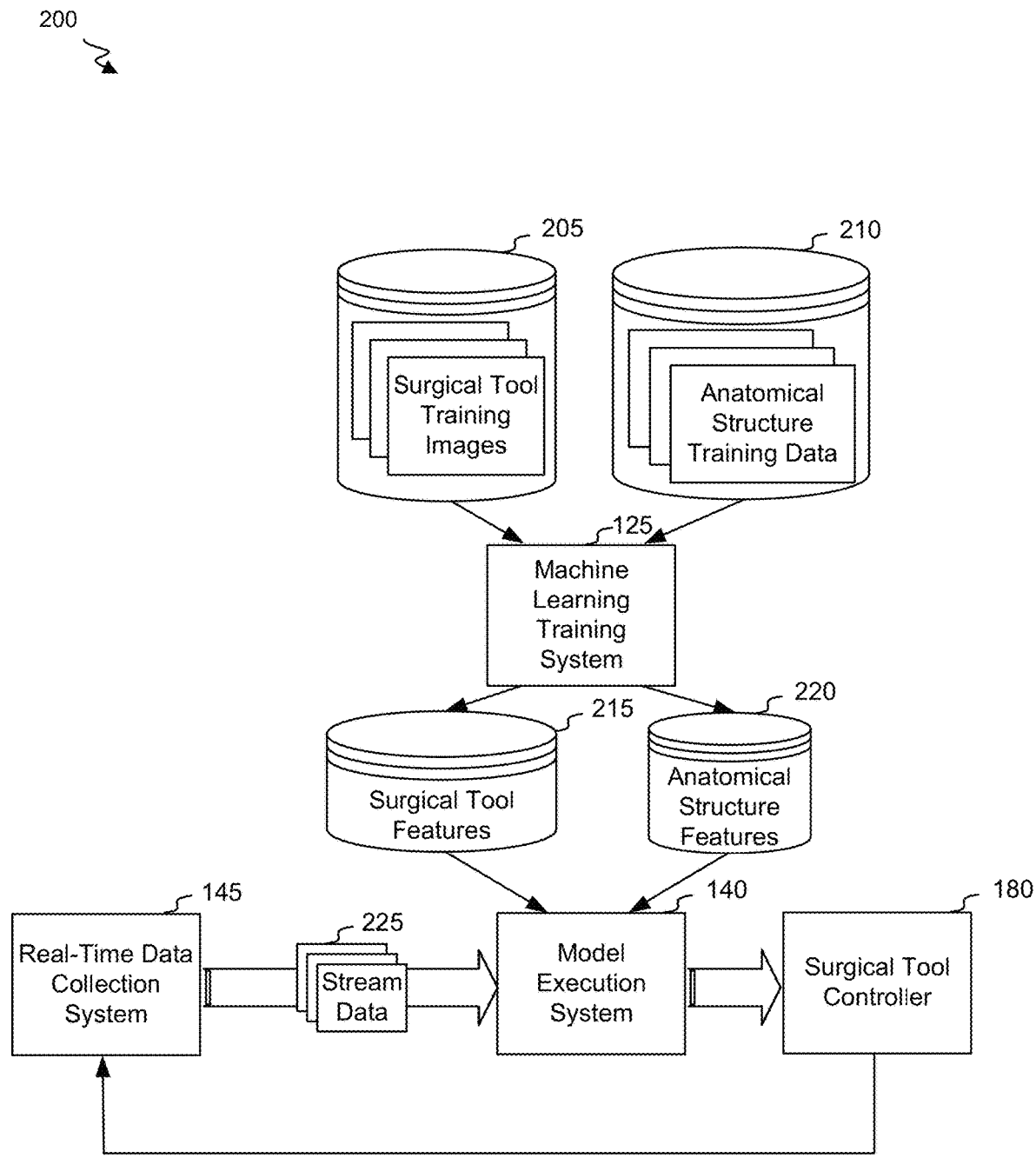
FIG. 2 shows a network for controlling or facilitating control of surgical tools during surgical procedures using computer-vision in accordance with some embodiments of the present disclosure.

FIG. 2 shows an image-processing flow 200 in accordance with some embodiments of the invention. In some implementations, surgical tool images 205 can be a data set of images (e.g., millions of images) fed into machine-learning training system 125 to train the machine-learning model to recognize surgical tools. For example, surgical tool images 205 can include images of various surgical tools from various angles. Similarly, anatomical structure training data 210 can be a data set of images (e.g., millions of images) fed into machine-learning training system 125 to train the machine-learning model to recognize anatomical structures, such as an organ (e.g., the liver), an "avoidance zone" near an iliac artery, and other suitable anatomical structures. Metadata can also be stored in association with each image. For example, the stored metadata can indicate, for each surgical tool image, one or more other associations (e.g., a procedural state of a surgical procedure, procedural type, operating-room identifier, surgeon identifier, and any other suitable association). It will be appreciated that machine-learning model can be trained to recognize other features within surgical tool images 205, in addition to or in lieu of surgical tools. For instance, machine-learning model can be trained to recognize surgeons, medical staff, lighting in the operating room, various operating settings of surgical tools, background details, and other suitable features associated with surgery.

Machine learning training system 125 can use surgical tool images 205 and anatomical structure training data 210 to train a machine-learning model. The machine-learning model can be defined based on one or more static and/or non-learnable parameters. The training can produce initial or updated values for each of a set of learnable parameters. For instance, the training can produce surgical tool features 215 and anatomical structure features 220. Surgical tool features 215 may be patterns of pixels that indicate a likelihood that the image includes a certain surgical tool. Surgical tool features 215 may be a data structure that stores the all of the various patterns or identifiers of the various patterns determined from training the machine-learning model. Similarly, anatomical structure features 220 may be patterns of pixels that indicate a likelihood that the image includes a certain anatomical structure. In some implementations, clearly defining anatomical structures may be achieved by supervised or unsupervised learning techniques. For instance, images in the data set of anatomical structure training data 210 may be labeled (e.g., by a medical professional). However, the present disclosure is not limited thereto. The anatomical structure training data 210 may be automatically classified using unsupervised or semi-supervised learning techniques.

Real-time data collection system 145 can avail real-time data (e.g., stream data 225) to model execution system 140. Stream data 225 can include (for example) a continuous or discrete feed from one or more imaging devices positioned within a procedural-performance environment. Stream data 225 can include one or more video streams and/or one or more image time series.

Model execution system 140 can analyze the stream data (e.g., by iteratively analyzing individual images, individual frames, or blocks of sequential images and/or frames) using the machine-learning model. The machine-learning model can be configured using surgical tool features 215 and anatomical structure features 220. A result of the analysis can include (e.g., for each iteration, image, frame or block) an identification of which (if any) objects are represented in the image and/or a position of each object included in the image. The identification of objects may include (for example) a vector of binary elements, with each element being associated with a particular object and a value for the element indicating whether the object was identified as being present. As another example, the identification of objects may include a vector of non-binary (e.g., discrete or continuous) elements, with each element being associated with a particular object and a value for the element indicating an inferred use, manipulation or object-state associated with the object (e.g., as identified based on position data). The objects may be surgical tools or anatomical structures.

In some implementations, the objects identified by model execution system 140 can be controlled in the physical space of the operating room by surgical tool controller 180. As a non-limiting example, model execution system 140 may generate an output indicating that an energy device (e.g., an energy device for laparoscopic diathermy) has been recognized within the field of view.

Figure 3:
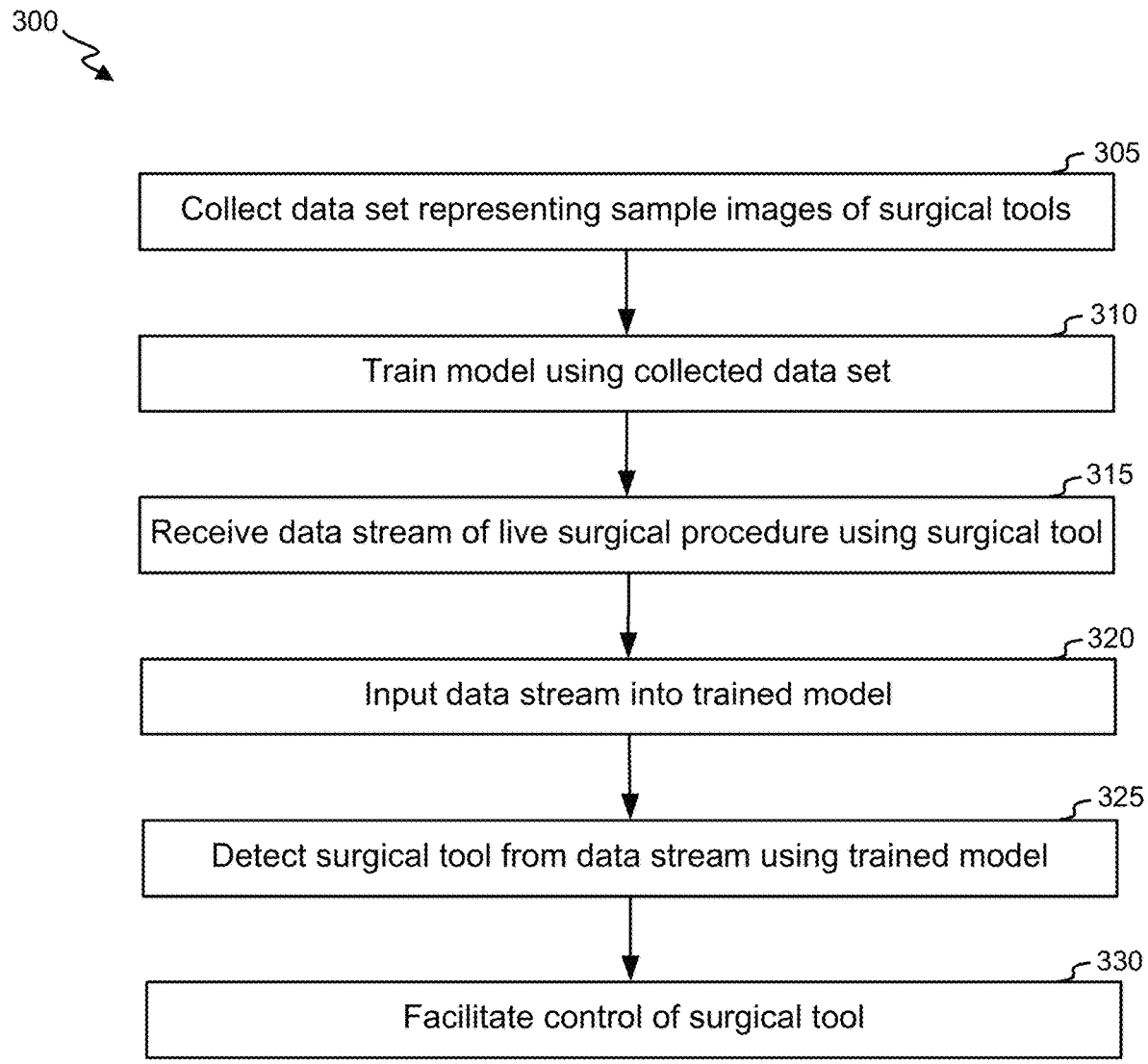
FIG. 3 is a flowchart illustrating an example process for controlling or facilitating control of surgical tools during surgical procedures using computer-vision in accordance with some embodiments of the present disclosure.

FIG. 3 is a flowchart illustrating example process 300 for controlling (or facilitating control of) surgical tools during surgical procedures using computer-vision in accordance with some embodiments of the present disclosure. Process 300 may be performed at least in part by any computing device illustrated in FIG. 1 or 2, including the computer-vision processing system (or any of its subcomponents) or the procedural control system (or any of its subcomponents). While process 300 may be performed by the computer-vision processing system, it will be appreciated that the present disclosure is not limited thereto.

Further, process 300 may be performed to enhance patient safety by controlling surgical tools using computer-vision. To illustrate, process 300 can be executed to process live video feed from a camera positioned to capture a surgical procedure. The computer-vision processing system can process the live video feed by feeding the pixels of image frames of the live video feed into a machine-learning model that is trained to recognize surgical tools or other objects, such as anatomical structures or faces of surgeons. The machine-learning model can be used to classify surgical tools detected within the field of view of the camera. When a surgical tool is detected within the camera's field of view, the computer-vision processing system may control (or facilitate control) the detected surgical tool. In some implementations, the recognition of a surgical tool by the computer-vision processing system can be used to interpret which stage (or phase) of a multistage or sequential-phase procedure is being performed at a given moment. The computer-vision processing system may control the surgical tool based on the detected stage or phase of the surgery. For example, if a particular surgical tool is only used during the second stage or phase of a surgery having multiple sequential stages or phases, then during that second stage of the surgery, the computer-vision processing system may disable all surgical tools except for the particular surgical tool used in that stage.

Process 300 begins at block 305, where the computer-vision processing system can collect a data set of sample images of surgical tools. In some implementations, the data set may include a plurality of images. The images may be captured using any image capturing device (e.g., a digital camera, a headset comprising a camera, a video camera, microscopes (e.g., for eye surgeries), and other suitable image capturing devices). The images may also be image frames of a video feed. The images may be retrieved from any data source (internal or external to a network, such as a data source accessible within a hospital network). The images may capture at least a portion of a surgical procedure, in which a surgical tool is used by a surgeon or other medical professional. The images collected in the data set may be sample images from previous surgeries, in which a surgical tool was used. The sample images may be used to train a machine-learning model to recognize surgical tools from new images, as described in greater detail below.

In some implementations, the sample images may include images of various objects other than surgical tools (or various objects in addition to surgical tools). For instance, the sample images may include images of anatomical structures. Non-limiting examples of anatomical structures may include stomachs, incisions, organs, ducts, gallbladders, appendix, and other suitable anatomical structures. The machine-learning model can be trained to recognize anatomical structures, as well as surgical tools. For example, the data set of the sample images may include thousands, hundreds of thousands, or millions of images in order to accurately train the machine-learning model. It will be appreciated that block 305 is not limited to the collection of sample images including surgical tools and anatomical structures. Images of any object can be collected and processed according to the embodiments described herein. For example, the data set of sample images may include images of a surgeon for facial recognition. As yet another example, the data set of sample images may include images of various stages of a particular surgery. The machine-learning model can then be trained to recognize the stage of the surgery from the live video feed.

At block 310, the computer-vision processing system can train a machine-learning model using the data set of sample images collected in block 305. One or more machine-learning algorithms may be executed on the collected data set to train the machine-learning model. For instance, an object recognition technique, such as a deep residual network (ResNet) may be used to classify surgical tools or anatomical structures from image pixels of a live video feed. Non-limiting examples of the machine-learning algorithms may include algorithms, such as an ensemble of multi-label classifiers (e.g., supervised or unsupervised learning), artificial neural networks (including backpropagation, Boltzmann machines, etc.), Bayesian statistics (e.g., Bayesian networks or knowledge bases), logistical model trees, support vector machines, information fuzzy networks, Hidden Markov models, hierarchical clustering (unsupervised), self-organizing maps, clustering techniques, and other suitable machine-learning techniques (supervised, semi-supervised, or unsupervised). The detected patterns can be used to define a model that can be used to recognize objects, such as surgical tools, within the sample images. In some implementations, the machine-learning algorithms may be applied to pixels of the data set of images to train the machine-learning model.

In some implementations, the machine-learning model may be trained to recognize and classify various objects, including surgical tools and anatomical structures. In some implementations, separate machine-learning models may be trained to recognize surgical tools and anatomical structures, respectively. The computer-vision processing system may also receive a feedback signal from a user (e.g., the surgeon) when the machine-learning model inaccurately recognizes a surgical tool. The feedback signal may be used to update the machine-learning model to improve the model's accuracy.

At block 315, the computer-vision processing system may receive one or more data streams of live video data. The live video data may be captured by a camera positioned to capture a live surgical procedure that uses a surgical tool. The one or more data streams may include a sequence of images (or image frames) of the live video that is captured within the field of view of a camera. The one or more data streams may be generated by the real-time data collection system (e.g., real-time data collection system 145), which may include a camera positioned in an operating room to capture a live video of a surgery.

In some implementations, the one or more data streams may be generated by a camera embedded or housed within a surgical tool, such as a laparoscope. The one or more data streams may capture a live video within a field of view of the laparoscope. For instance, if the laparoscope has been inserted into a patient through a small incision in the patient's abdomen, then the laparoscope may capture a portion of the patient's organs. The computer-vision processing system can receive and process a first data stream generated by a camera positioned in the operating room to capture the surgical procedure and a second data stream generated by a laparoscope inserted into a patient.

At block 320, the one or more data streams generated by the camera or the laparoscope may be inputted into the trained machine-learning model. For instance, the data stream may be fed into the model execution system (e.g., model execution system 140) of the computer-vision processing system. Inputting the one or more data streams into the machine-learning model may include automatically determining whether any pixels within the image frames of the one or more data streams are recognizable as being a part of a surgical tool or anatomical structure. The trained model may be configured to recognize patterns of pixels that represent features of a surgical tool or an anatomical structure.

At block 325, a result of inputting the one or more data streams into the machine-learning model may be a detection of a surgical tool or anatomical structure (provided that the surgical tool or anatomical structure is within the field of view of the camera). For example, if the pixels of a sequence of images frames included a laparoscopic stapler, the machine-learning model may be trained to recognize those pixels as being part of the laparoscopic stapler. Detecting the surgical tool may be performed by utilizing the machine-learning model to recognize the surgical tool from the sequence of images of the live video. Further, the computer-vision processing system may interpret the detection of the surgical tool from the sequence of images as an indication that the surgical tool is within the field of view of the camera. Conversely, the computer-vision processing system may interpret the lack of a detection of any pixels representing a surgical tool as indicating that the surgical tool is not or no longer within the field of view of the camera.

At block 330, the computer-vision processing system can control (or facilitate control) of the surgical tool detected as being within the field of view of the camera. A surgical tool may be capable of performing one or more functions. For example, a laparoscopic stapler can fire a staple or suture. In some implementations, the functionality of the surgical tool may be controlled in response to an output signal from the procedural control system of the computer-vision processing system. Non-limiting examples of controlling the functionality of the surgical tool may include enabling the surgical tool to perform the function (e.g., enabling the laparoscopic stapler to fire a staple), disabling the ability of the surgical tool to perform the function (e.g., disabling the stapling functionality of the laparoscopic stapler), adjusting the magnitude of the function (e.g., increasing or decreasing a vacuum pressure, but not enabling or disabling the vacuum function altogether), causing the device to output an audible or visual signal (e.g., causing a display screen on a digital laparoscopic device to present certain text, such as "Alert— Avoidance Zone Detected"), adjusting a position or setting of a surgical tool, disabling a set of functions from being performed and enabling a different set of functions to be performed, and any other suitable modification.

It will be appreciated that other devices within the operating room may be controlled in addition to or in lieu of controlling the surgical tool. For example, the lighting within the operating room may be controlled if the computer-vision processing system detects that a laparoscopic stapler is about to be inserted into an incision in the patient's abdomen. It will also be appreciated that the position of or a physical setting of a surgical tool may be modified or adjusted based on an output of the machine-learning model. For example, the angle of the cutting arms of a laparoscopic scissor may be adjusted towards or away from a detected anatomical structure. It will also be appreciated that the functionality of a plurality of surgical tools may be controlled, even if only some (but not all) of the plurality of surgical tools are detected within the camera's field of view. For example, if the live video of a laparoscope within a patient captures a hematoma (e.g., localized bleeding outside of blood vessels), the computer-vision processing system can detect the hematoma using the embodiments described herein and disable all surgical tools being used for the procedural (or enable only the surgical tools necessary to address the hematoma and disable the other surgical tools).

Figure 4:
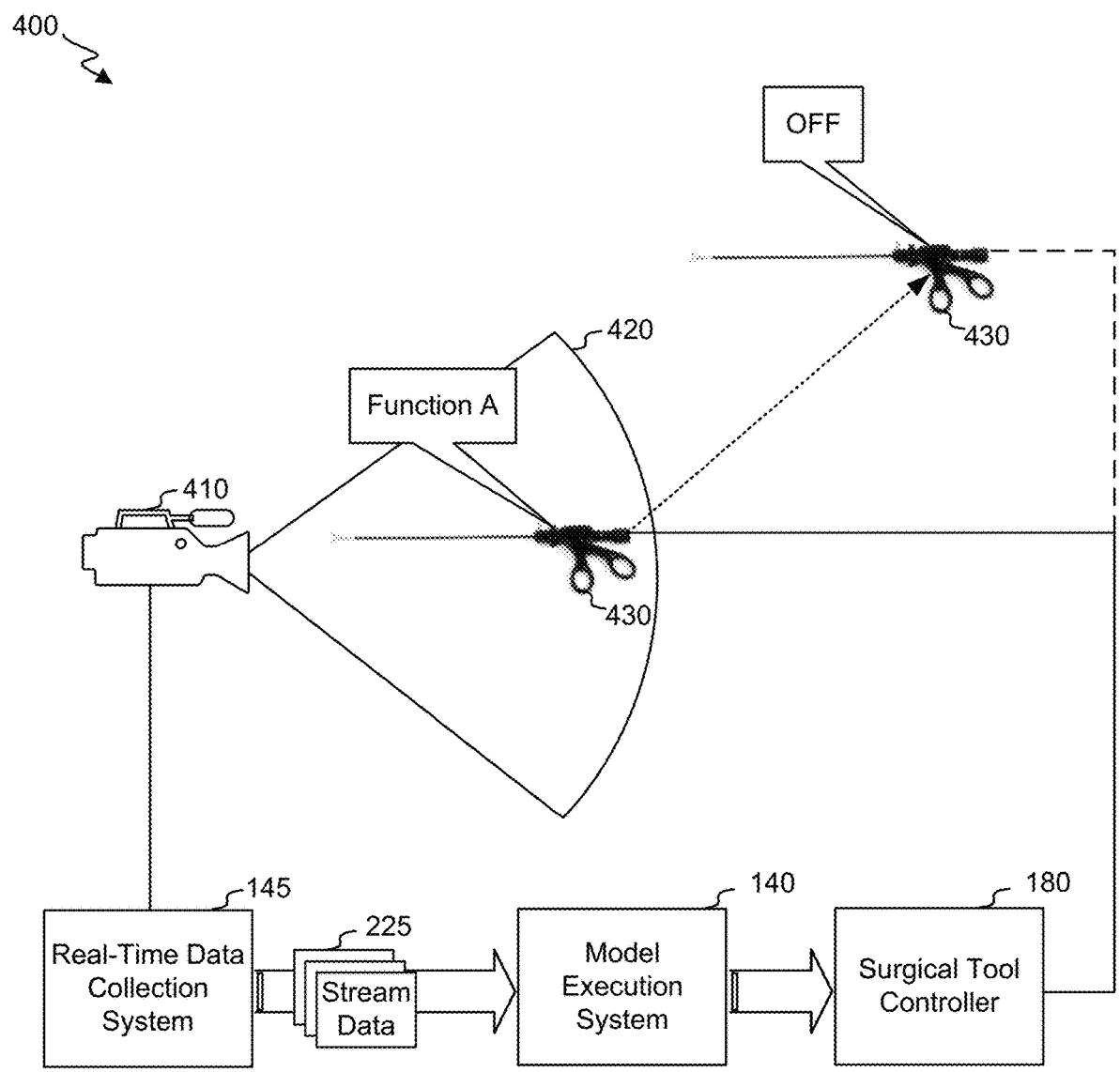
FIG. 4 shows an example process flow for controlling or facilitating control of an energy device controlling ultrasonic shears in accordance with some embodiments of the present disclosure.

FIG. 4 shows example process flow 400 for controlling (or facilitating control of) an energy device coupled to ultrasonic shears in accordance with some embodiments of the present disclosure. Process flow 400 begins with real-time data collection system 145 capturing live video of a surgical procedure, such as a cholecystectomy (i.e., surgical removal of the gallbladder). The surgical procedure may be performed using several surgical tools, including at least ultrasonic shears 430 (shown in FIG. 4) powered by an energy device. Additionally, video camera 410 may be positioned within an operating room to capture the surgical procedure in real-time. Video camera 410 may capture live video within field of view 420. Ultrasonic shears 430 may be capable of performing a cutting function (i.e., Function A). Further, video camera 410 may generate one or more data streams representing a live video feed, which is transmitted to real-time data collection system 145. Real-time data collection system 145 may process the video feed from video camera 410 further transmit stream data 225 to model execution system 140.

Model execution system 140 may input stream data 225 into the trained machine-learning model. In this example, the machine-learning learning model may be trained to recognize pixels that represent at least a portion of a surgical tool. If the ultrasonic shears 430 is within the field of view 420, then at least a portion of the ultrasonic shears 430 would be represented in stream data 225. The machine-learning model may recognize the pixels showing the jaws and the shears shaft as being a part of ultrasonic shears 430. Thus, the output of the machine-learning model may indicate that the live video can be interpreted as including ultrasonic shears within field of view 420. Model execution system 140 can then transmit an output command signal to surgical tool controller 180, which can facilitate controlling the ultrasonic shears 430. For example, if ultrasonic shears 430 are detected as being within field of view 420, then surgical tool controller 180 to cause the ultrasonic shears 430 to be enabled to perform energy dissecting or sealing functions. However, if ultrasonic shears 430 are not detected as being within field of view 420 (e.g., if the output of model execution system 140 does not indicate the identification of ultrasonic shears 430 within field of view 420), then surgical tool controller 180 can transmit a command signal to ultrasonic shears 430 that causes the tool to be disabled.

Figure 5:
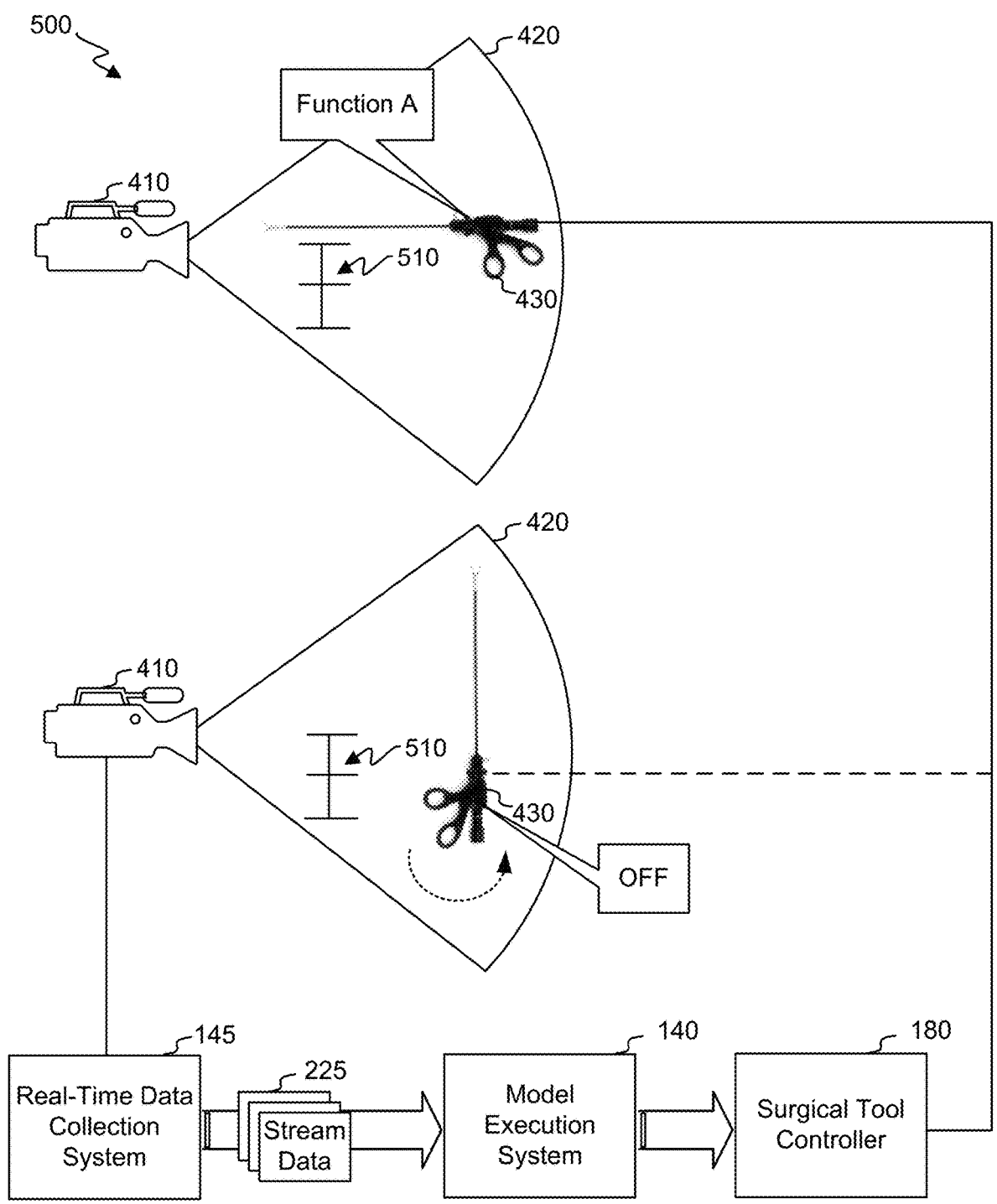
FIG. 5 shows yet another example process flow for controlling or facilitating control of an energy device controlling ultrasonic shears in accordance with some embodiments of the present disclosure.

FIG. 5 shows yet another example process flow 500 for controlling (or facilitating control of) ultrasonic shears 430 in accordance with some embodiments of the present disclosure. Continuing with the example of FIG. 4, the computer-assisted surgical system described herein can control (or facilitate the control of) ultrasonic shears 430 based on the articulation, position, or orientation of ultrasonic shears 430 in relation to anatomical structure 510. Video camera 410 may capture live video of a surgical procedure, just as in FIG. 4. In the example illustrated in FIG. 5, the surgical procedure may be a single-port entry procedure, in which surgery is performed through a single incision in the patient's navel. Many surgeries can be performed using a single incision, including, for example, donor nephrectomy, cystectomy, and cryoablation.

In FIG. 5, anatomical structure 510 may be the single incision made to the patient's navel. While not shown in FIG. 5, a trocar may be inserted into anatomical structure 510 into which other surgical tools can be inserted, such as a laparoscope (also not shown) and ultrasonic shears 430. Real-time data collection system 145 may receive and process the one or more data streams from video camera 410. Real-time data collection system 145 may generate stream data 225, which includes the one or more data streams of the live video stream.

Model execution system 140 may receive stream data 225 and input stream data 225 into the machine-learning model. For example, model execution system 140 may individually input each image frame of the live video included in stream data 225 into the machine-learning model. The machine-learning model may be trained to recognize surgical tools, similar to the machine-learning model described in FIG. 4. Additionally, either the same machine-learning model or another machine-learning model may be trained to recognize anatomical structures. For example, a data set of sample images of single incisions in patients' navels may be used to train the machine-learning model to recognize single-port entry surgeries in new images.

When model execution system 140 receives image frames including pixels that show ultrasonic shears 430 pointed upwards (towards the ceiling, and thus, angled away from anatomical structure 510), model execution system 140 may generate an output that is transmitted to surgical tool controller 180 and that causes surgical tool controller 180 to disable ultrasonic shears 430 from cutting. Advantageously, when both anatomical structure 510 and ultrasonic shears 430 are detected within field of view 420, the computer-assisted surgical system can further determine whether ultrasonic shears 430 is in a predefined articulation, position, or orientation in relation to anatomical structure 510. If, as described above and illustrated at the lower portion of FIG. 5, ultrasonic shears 430 are angled away from anatomical structure 510, then the computer-assisted surgical system may cause ultrasonic shears 430 to be disabled (through model execution system 140 and surgical tool controller 180). Further, if, as illustrated at the upper portion of FIG. 5, ultrasonic shears 430 are angled towards anatomical structure 510 (or otherwise detected as being within a predefined angle range of anatomical structure 510 or within the trocar described above), then the computer-assisted surgical system may cause ultrasonic shears 430 to be enabled to engage the cutting function (also through model execution system 140 and surgical tool controller 180).

While FIGS. 4-5 illustrate that the data streams are generated by video camera 410, it will be appreciated that the one or more data streams may include at least one data stream from a laparoscope. The machine-learning model may be trained to detect anatomical structures within the patient from the image frames generated by the laparoscope. For example, in a laparoscopic sleeve gastrectomy, a laparoscope may be inserted into the patient through an incision. The machine-learning model may process each image frame from the laparoscope to determine whether the pixels within the image frames include an anatomical structure, such as the patient's liver. It will also be appreciated that the laparoscope may detect vapor in the abdomen. In this case, the machine-learning model may be trained to detect vapor by applying machine-learning algorithms to a data set (e.g., thousands, hundreds of thousands, or millions of images) of sample images of vapor in abdomens. If vapor is detected, then the computer-assisted surgical system may cause a vacuum tube to suction out the vapor.

Additionally, while FIGS. 4-5 illustrate a single surgical tool (i.e., ultrasonic shears 430), it will be appreciated that multiple surgical tools may be used during a surgery. The computer-assisted surgical system can detect each individual surgical tool within field of view 420. Further, the computer-assisted surgical system can also individually control each surgical tool detected within field of view 420. The computer-assisted surgical system can also control surgical tools that are not detected within field of view 420, but known to the computer-assisted surgical system as being used during the surgical procedure. For example, in some cases, the computer-assisted surgical system can determine which surgery is being performed from user input. The user input can indicate the type of surgery being performed and/or the surgical tools to be used during the surgery. In some cases, the computer-assisted surgical system can automatically detect which surgery is about to be performed or is being performed by inputting the image frames of the live video feed into the machine-learning model. For example, the image frames may include pixels showing the various surgical tools that will be used during the surgery, and accordingly, the computer-assisted surgical system can identify a set of candidate surgeries that could be performed based on the detected tools. It will also be appreciated that the computer-assisted surgical system can be connected to a hospital network. In this case, the computer-assisted surgical system can retrieve a cloud-based calendar for the operating room to determine which surgery is being performed, and thus, also determine which surgical tools will be used during the surgery. It will be appreciated that the computer-assisted surgical system can detect an action being performed (with or without a surgical tool), and control secondary or auxiliary surgical tools based on the detection of the action. For example, in a laparoscopic cholecystectomy, energy devices may be disabled by the computer-assisted surgical system when the computer-assisted surgical system detects that a cystic duct is being clipped.

Figure 6:
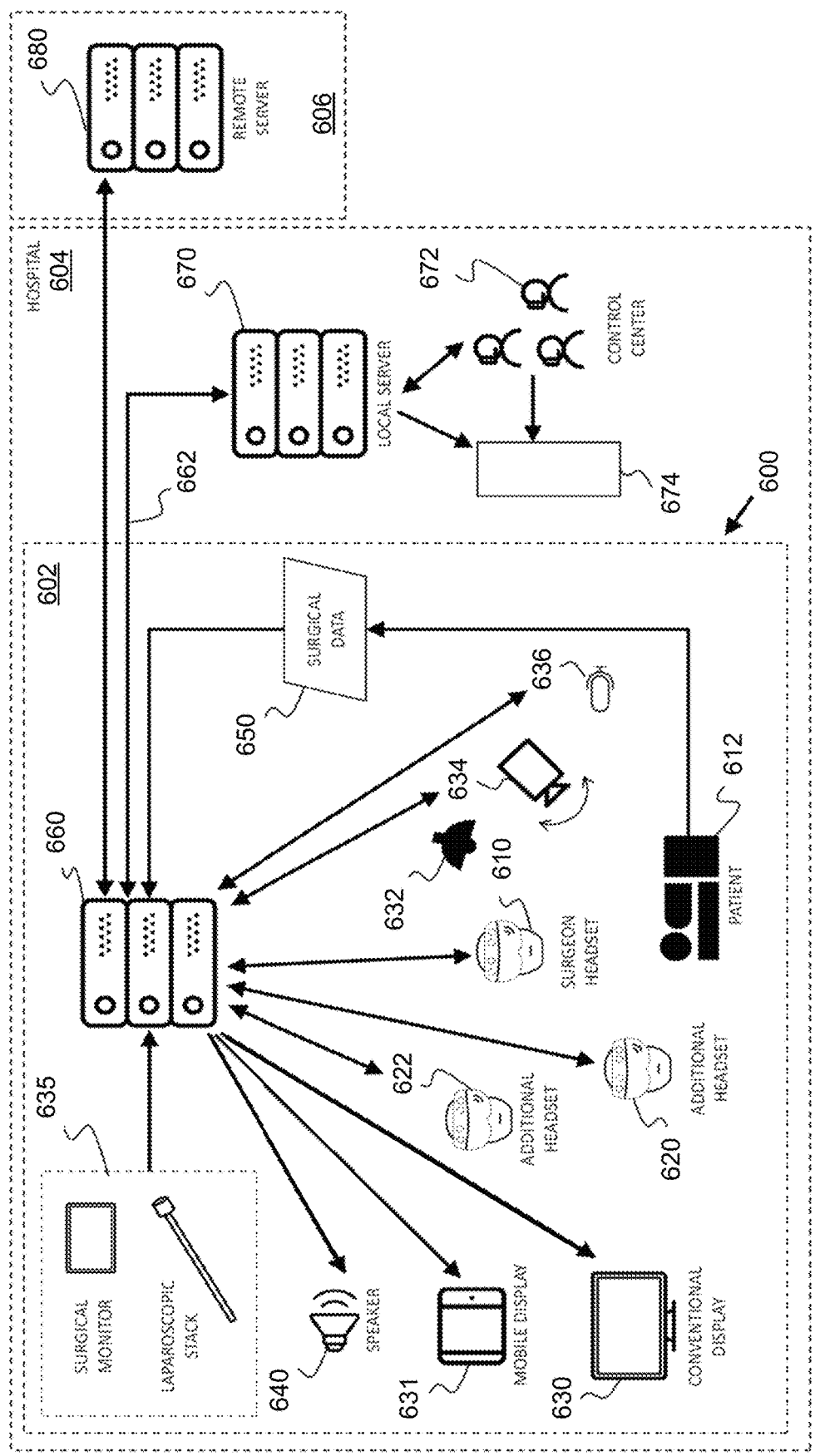
FIG. 6 shows an embodiment of a system for collecting data and producing an electronic output in accordance with some embodiments of the present disclosure.

FIG. 6 shows an embodiment of a system 600 for collecting live or previously collected data and/or presenting data corresponding to state detection, object detection and/or object characterization performed based on executing a multi-dimensional artificial intelligence. System 600 can include one or more components of a procedural control system.

Computing device 660 can be placed inside the operating room or worn by a member of the operating room (e.g., surgeon, medical assistant, nurse, etc.) to capture data steams (e.g., video content) of the surgical environment. The data can include image data (which can, in some instances, include video data) and/or other types of data. For example, in laparoscopic or microsurgery procedures, computing device 660 may capture data streams from video sources, such as a laparoscopic stack or a surgical monitor (collectively, 635), with video outputs. The data can be transmitted to a computing device 660 via a wired connection or a wireless connection. In some embodiments, the computing device 660 may be wirelessly connected. The computing device 660 can collect data from a number of sources including (for example) a surgeon mounted headset 610, a first additional headset 620, a second additional headset 622, surgical data 650 associated with a patient 612, an operating room camera 634, and an operating room microphone 636, and additional operating room tools not illustrated in FIG. 6. Local server 670 receives the data from the computing device 660 over a connection 662 (e.g., wired or wireless) and a surgical data structure from a remote server 680.

In some instances, the computing device 660 can process the data (e.g., to identify and/or characterize a presence and/or position of one or more tools using a trained machine-learning model, to identify a procedural state using a trained machine-learning model or to train a machine-learning model). The computing device 660 can process the metadata corresponding to a procedural state identified as corresponding to live data and generate real-time guidance information for output to the appropriate devices. Also, local server 670 can include one or more components of the machine-learning processing system. Local server 670 can process the metadata corresponding to a procedural state identified as corresponding to live data and generate real-time guidance information for output to the control center 672.

The computing device 660 can be in contact with and synced with a remote server 680. In some embodiments, remote server 680 can be located in the cloud 606. In some embodiments, remote server 680 can process the live data (e.g., to identify and/or characterize a presence and/or position of one or more tools using a trained machine-learning model, to identify a procedural state using a trained machine-learning model or to train a machine-learning model). Remote server 680 can include one or more components of the machine-learning processing system. Remote server 680 can process the metadata corresponding to a procedural state identified as corresponding to live data and generate real-time guidance information for output to the appropriate devices in operating room 602.

A global bank of surgical procedures, described using surgical data structures, may be stored at remote server 680. Therefore, for any given surgical procedure, there is the option of running system 600 as a local, or cloud-based system. The computing device 660 can create a surgical dataset that records data collected during the performance of a surgical procedure. The computing device 660 can analyze the surgical dataset or forward the surgical dataset to remote server 680 upon the completion of the procedure for inclusion in a global surgical dataset. In some embodiments, the computing device 660 can anonymize the surgical dataset in real-time or up the completion of the procedure. System 600 can integrate data from the surgical data structure and sort guidance data appropriately in the operating room using additional components.

In certain embodiments, surgical guidance, retrieved from the surgical data structure, may include more information than necessary to assist the surgeon with situational awareness. The system 600 may determine that the additional operating room information may be more pertinent to other members of the operating room and transmit the information to the appropriate team members. Therefore, in certain embodiments, system 600 provides surgical guidance to more components than a conventional display 630.

In certain embodiments, surgical guidance, retrieved from the surgical data structure, may include more information than necessary to assist the surgeon with situational awareness. The system 600 may determine that the additional operating room information may be more pertinent to other members of the operating room and transmit the information to the appropriate team members. Therefore, in certain embodiments, system 600 provides surgical guidance to more components than a conventional display 630.

In the illustrated embodiment, mobile devices 631, such as smartphones and tablets, and wearable devices, such as a surgeon's headset 610, a first additional headset 620 and a second additional headset 622, are included in the system 600. Other members of the operating room team may benefit from receiving information and surgical guidance derived from the surgical data structure on the mobile and wearable devices. For example, a surgical nurse wearing first additional headset 620 or having a mobile device 631 in the close vicinity may benefit from guidance related to procedural steps and possible equipment needed for impending steps. An anesthetist wearing second additional headset 622 or having a mobile display 631 in the close vicinity may benefit from seeing the patient vital signs in the field of view. In addition, the anesthetist may be the most appropriate user to receive the real-time risk indication as one member of the operating room slightly removed from surgical action.

Various peripheral devices can further be provided, such as conventional displays 630, transparent displays that may be held between the surgeon and patient, ambient lighting 632, one or more operating room cameras 634, one or more operating room microphones 636, speakers 640 and procedural step notification screens placed outside the operating room to alert entrants of critical steps taking place. These peripheral components can function to provide, for example, state-related information. In some instances, one or more peripheral devices can further be configured to collect image data.

The computing device 660 may use one or more communications networks to communicate with operating room devices including (for example) wired connections (e.g., Ethernet connections) or various wireless protocols, such as IrDA™, Bluetooth™, Zigbee™ Ultra-Wideband, and/or Wi-Fi. In some embodiments, existing operating room devices can be integrated with system 600. To illustrate, once a specific procedural location is reached, automatic functions can be set to prepare or change the state of relevant and appropriate medical devices to assist with impending surgical steps. For example, operating room lighting 632 can be integrated into system 600 and adjusted based on impending surgical actions indicated based on a current procedural state.

In some embodiments, system 600 may include a centralized hospital control center 672 and a central hospital local server 670 associated with hospital 604. The control center 672 through the hospital local server 670 may be connected to one, more or all active procedures and coordinate actions in critical situations as a level-headed, but skilled, bystander. Control center 672 may be able to communicate with various other users via user-specific devices 674 (e.g., by causing a visual or audio stimulus to be presented at a headset) or more broadly (e.g., by causing audio data to be output at a speaker in a given room 602).

In some instances, methods and systems are provided for performing anonymization of one or more data streams from the surgical procedure in a real-time process or an offline process. In some embodiments, the computing device 660 or a remote server 680 can anonymize and store the one or more data streams from a surgical procedure. Data streams (e.g., video streams) from a surgical procedure contain sensitive or confidential information such as patient identification, voice data, facial features, and other sensitive personal information about the patient and/or operating room personnel. In some embodiments, the method includes anonymizing and protecting the identity of all medical professionals, patients, distinguishing objects or features in a medical, clinical or emergency unit. The methods and systems can detect facial features, objects, or features in a medical, clinical or emergency unit and distort or blur or colorize (e.g., black) or remove the image of the distinguishing element. In some embodiments, the extent of the distortion/blur/colorization is limited to a localized area, frame by frame, to the point where identity is protected without limiting the quality of the analytics.

Specific details are given in the above description to provide a thorough understanding of the embodiments or implementations. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

What is claimed is:

1. A computer-implemented method comprising:
   collecting a data set including a plurality of images, each image of the plurality of images capturing a portion of a surgical procedure, and the portion of the surgical procedure being performed using a surgical tool;
   training a model using the data set, the model being trained to recognize surgical tools from image data by inputting the data set into one or more machine-learning algorithms;
   receiving one or more data streams, each of the one or more data streams having been generated at and received from an electronic device configured and positioned to capture live video within a field of view during a particular surgical procedure being performed using one or more surgical tools, and the one or more data streams including a sequence of images of the live video within the field of view;
   inputting the one or more data streams into the trained model;
   in response to inputting the one or more data streams into the trained model, detecting a surgical tool from the sequence of images of the one or more data streams, the surgical tool being configured to perform a primary function, the detection of the surgical tool being performed by utilizing the model to recognize the surgical tool from the sequence of images of the live video, and the detection of the surgical tool indicating that the surgical tool is within the field of view;
   in response to detecting the surgical tool within the field of view,
   outputting one or more commands for controlling the surgical tool to perform the primary function, the detection of the surgical tool from the sequence of images of the live video causing the surgical tool to be enabled to perform the primary function, wherein detecting that the surgical tool is no longer within the field of view causes the surgical tool to cease or regulate performance of the primary function; and
   the surgical tool is configured to perform a plurality of functions, wherein the plurality of functions includes the primary function and a secondary function, wherein the primary function is different from the secondary function, and wherein detecting that the surgical tool is no longer within the field of view of the electronic device causes the surgical tool to be enabled to perform the secondary function.

2. The computer-implemented method of claim 1, further comprising:
   determining that the surgical tool is no longer detected from the sequence of images of the live video; and
   facilitating controlling the surgical tool to cease performing the primary function or to regulate performance of the primary function while the surgical tool is not within the field of view of the electronic device, wherein when the surgical tool is not detected by the electronic device, the surgical tool is no longer enabled to perform the primary function or the performance of the primary function is regulated.

3. The computer-implemented method of claim 1, further comprising:
   detecting an anatomical structure from the sequence of images of the live video, the anatomical structure being detected by utilizing the model to recognize the anatomical structure from the sequence of images;
   in response to detecting the anatomical structure, determining whether the surgical tool is oriented in a specific articulation, position, or orientation in relation to the anatomical structure;
   when the surgical tool is not in the specific articulation, position, or orientation in relation to the anatomical structure, automatically controlling the surgical tool to cease performing the primary function or to regulate performance of the primary function; and
   when the surgical tool is in the specific articulation, position, or orientation in relation to the anatomical structure, automatically controlling the surgical tool to perform the primary function or to regulate performance of the primary function.

4. The computer-implemented method of claim 1, further comprising:
   detecting an object from the sequence of images of the live video, the object being detected by utilizing the model to recognize the object from the sequence of images;
   determining a distance between the surgical tool and the object;
   comparing the determined distance to a threshold distance;
   when the determined distance is greater than or equal to the threshold distance, automatically controlling the surgical tool to cease performing the primary function or to regulate performance of the primary function; and
   when the determined distance is less than the threshold distance, automatically controlling the surgical tool to perform the primary function or to regulate performance of the primary function.

5. The computer-implemented method of claim 1, further comprising:
   identifying that the particular surgical procedure comprises a plurality of sequential phases;
   determining that the primary function is to be performed during a phase of the plurality of sequential phases of the particular surgical procedure;
   detecting that the surgical procedure is in the phase of the plurality of sequential phases, the phase being detected by utilizing the model to recognize the phase from the sequence of images; and
   in response to detecting that the surgical procedure is in the phase of the plurality of sequential phases, facilitating controlling the surgical tool to perform the primary function.

6. The computer-implemented method of claim 5, further comprising:
   detecting that the surgical procedure is in next phase of the plurality of sequential phases, the next phase being detected by utilizing the model to recognize the next phase from the sequence of images; and
   in response to detecting that the surgical procedure is in the next phase, facilitating controlling the surgical tool to cease performing the primary function or to regulate performance of the primary function.

7. A system, comprising:
   one or more data processors; and
   a non-transitory computer-readable storage medium containing instructions which, when executed on the one or more data processors, cause the one or more data processors to perform operations including:
   collecting a data set including a plurality of images, each image of the plurality of images capturing a portion of a surgical procedure, and the portion of the surgical procedure being performed using a surgical tool;

training a model using the data set, the model being trained to recognize surgical tools from image data by inputting the data set into one or more machine-learning algorithms;

receiving one or more data streams, each of the one or more data streams having been generated at and received from an electronic device configured and positioned to capture live video within a field of view during a particular surgical procedure being performed using one or more surgical tools, and the one or more data streams including a sequence of images of the live video within the field of view; inputting the one or more data streams into the trained model;

in response to inputting the one or more data streams into the trained model, detecting a surgical tool from the sequence of images of the one or more data streams, the surgical tool being configured to perform a primary function, the detection of the surgical tool being performed by utilizing the model to recognize the surgical tool from the sequence of images of the live video, and the detection of the surgical tool indicating that the surgical tool is within the field of view;

in response to detecting the surgical tool within the field of view, outputting one or more commands for controlling the surgical tool to perform the primary function, the detection of the surgical tool from the sequence of images of the live video causing the surgical tool to be enabled to perform the primary function, wherein detecting that the surgical tool is no longer within the field of view causes the surgical tool to cease or regulate performance of the primary function; and the surgical tool is configured to perform a plurality of functions, wherein the plurality of functions includes the primary function and a secondary function, wherein the primary function is different from the secondary function, and wherein detecting that the surgical tool is no longer within the field of view of the electronic device causes the surgical tool to be enabled to perform the secondary function.

8. The system of claim 7, wherein the operations further comprise:

determining that the surgical tool is no longer detected from the sequence of images of the live video; and facilitating controlling the surgical tool to cease performing the primary function or to regulate performance of the primary function while the surgical tool is not within the field of view of the electronic device, wherein when the surgical tool is not detected by the electronic device, the surgical tool is no longer enabled to perform the primary function or the performance of the primary function is regulated.

9. The system of claim 7, wherein the operations further comprise:

detecting an anatomical structure from the sequence of images of the live video, the anatomical structure being detected by utilizing the model to recognize the anatomical structure from the sequence of images;

detecting an anatomical structure from the sequence of images of the live video, the anatomical structure being detected by utilizing the model to recognize the anatomical structure from the sequence of images;

in response to detecting the anatomical structure, determining whether the surgical tool is oriented in a specific articulation, position, or orientation in relation to the anatomical structure;

when the surgical tool is not in the specific articulation, position, or orientation in relation to the anatomical structure, automatically controlling the surgical tool to cease performing the primary function or to regulate performance of the primary function; and when the surgical tool is in the specific articulation, position, or orientation in relation to the anatomical structure, automatically controlling the surgical tool to perform the primary function or to regulate performance of the primary function.

10. The system of claim 7, wherein the operations further comprise:

detecting an object from the sequence of images of the live video, the object being detected by utilizing the model to recognize the object from the sequence of images;

determining a distance between the surgical tool and the object;

comparing the determined distance to a threshold distance;

when the determined distance is greater than or equal to the threshold distance, automatically controlling the surgical tool to cease performing the primary function or to regulate performance of the primary function; and when the determined distance is less than the threshold distance, automatically controlling the surgical tool to perform the primary function or to regulate performance of the primary function.

11. The system of claim 7, wherein the operations further comprise:

identifying that the particular surgical procedure comprises a plurality of sequential phases;

determining that the primary function is to be performed during a phase of the plurality of sequential phases of the particular surgical procedure;

detecting that the surgical procedure is in the phase of the plurality of sequential phases, the phase being detected by utilizing the model to recognize the phase from the sequence of images; and in response to detecting that the surgical procedure is in the phase of the plurality of sequential phases, facilitating controlling the surgical tool to perform the primary function.

12. The system of claim 11, wherein the operations further comprise:

detecting that the surgical procedure is in next phase of the plurality of sequential phases, the next phase being detected by utilizing the model to recognize the next phase from the sequence of images; and in response to detecting that the surgical procedure is in the next phase, facilitating controlling the surgical tool to cease performing the primary function or to regulate performance of the primary function.

13. A computer-program product tangibly embodied in a non-transitory machine-readable storage medium, including instructions configured to cause a data processing apparatus to perform operations including:

collecting a data set including a plurality of images, each image of the plurality of images capturing a portion of a surgical procedure, and the portion of the surgical procedure being performed using a surgical tool;

training a model using the data set, the model being trained to recognize surgical tools from image data by inputting the data set into one or more machine-learning algorithms;

receiving one or more data streams, each of the one or more data streams having been generated at and received from an electronic device configured and positioned to capture live video within a field of view during a particular surgical procedure being performed using one or more surgical tools, and the one or more data streams including a sequence of images of the live video within the field of view;

inputting the one or more data streams into the trained model;

in response to inputting the one or more data streams into the trained model, detecting a surgical tool from the sequence of images of the one or more data streams, the surgical tool being configured to perform a primary function, the detection of the surgical tool being performed by utilizing the model to recognize the surgical tool from the sequence of images of the live video, and the detection of the surgical tool indicating that the surgical tool is within the field of view;

in response to detecting the surgical tool within the field of view, outputting one or more commands for controlling the surgical tool to perform the primary function, the detection of the surgical tool from the sequence of images of the live video causing the surgical tool to be enabled to perform the primary function, wherein detecting that the surgical tool is no longer within the field of view causes the surgical tool to cease or regulate performance of the primary function; and the surgical tool is configured to perform a plurality of functions, wherein the plurality of functions includes the primary function and a secondary function, wherein the primary function is different from the secondary function, and wherein detecting that the surgical tool is no longer within the field of view of the electronic device causes the surgical tool to be enabled to perform the secondary function.

14. The computer-program product of claim 13, wherein the operations further comprise:

determining that the surgical tool is no longer detected from the sequence of images of the live video; and facilitating controlling the surgical tool to cease performing the primary function or to regulate performance of the primary function while the surgical tool is not within the field of view of the electronic device, wherein when the surgical tool is not detected by the electronic device, the surgical tool is no longer enabled to perform the primary function or the performance of the primary function is regulated.

15. The computer-program product of claim 13, wherein the operations further comprise:

detecting an anatomical structure from the sequence of images of the live video, the anatomical structure being detected by utilizing the model to recognize the anatomical structure from the sequence of images;

in response to detecting the anatomical structure, determining whether the surgical tool is oriented in a specific articulation, position, or orientation in relation to the anatomical structure;

when the surgical tool is not in the specific articulation, position, or orientation in relation to the anatomical structure, automatically controlling the surgical tool to cease performing the primary function or to regulate performance of the primary function; and when the surgical tool is in the specific articulation, position, or orientation in relation to the anatomical structure, automatically controlling the surgical tool to perform the primary function or to regulate performance of the primary function.

16. The computer-program product of claim 13, wherein the operations further comprise:

detecting an object from the sequence of images of the live video, the object being detected by utilizing the model to recognize the object from the sequence of images;

determining a distance between the surgical tool and the object;

comparing the determined distance to a threshold distance;

when the determined distance is greater than or equal to the threshold distance, automatically controlling the surgical tool to cease performing the primary function or to regulate performance of the primary function; and when the determined distance is less than the threshold distance, automatically controlling the surgical tool to perform the primary function or to regulate performance of the primary function.

17. The computer-program product of claim 13, wherein the operations further comprise:

identifying that the particular surgical procedure comprises a plurality of sequential phases;

determining that the primary function is to be performed during a phase of the plurality of sequential phases of the particular surgical procedure;

detecting that the surgical procedure is in the phase of the plurality of sequential phases, the phase being detected by utilizing the model to recognize the phase from the sequence of images; and in response to detecting that the surgical procedure is in the phase of the plurality of sequential phases, facilitating controlling the surgical tool to perform the primary function.

* * * * *